United States Patent
Chang et al.

(10) Patent No.: US 9,248,139 B2
(45) Date of Patent: Feb. 2, 2016

(54) CO-PROCESSING METHOD AND FORMULATIONS FOR HIV ATTACHMENT INHIBITOR PRODRUG COMPOUND AND EXCIPIENTS

(71) Applicant: Bristol-Myers Squibb Company, Princeton, NJ (US)

(72) Inventors: Shih-Ying Chang, Princeton, NJ (US); Donald Kientzler, Millstone Township, NJ (US); Deniz Erdemir, Robbinsville, NJ (US); San Kiang, Morristown, NJ (US); Tamar Rosenbaum, Lakewood, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 10 days.

(21) Appl. No.: 13/716,306

(22) Filed: Dec. 17, 2012

(65) Prior Publication Data

US 2013/0164345 A1    Jun. 27, 2013

Related U.S. Application Data

(60) Provisional application No. 61/578,689, filed on Dec. 21, 2011.

(51) Int. Cl.
*A61K 31/675* (2006.01)
*A61K 9/14* (2006.01)
*A61K 9/20* (2006.01)

(52) U.S. Cl.
CPC .............. *A61K 31/675* (2013.01); *A61K 9/14* (2013.01); *A61K 9/146* (2013.01); *A61K 9/2054* (2013.01); *A61K 9/2095* (2013.01)

(58) Field of Classification Search
USPC ........................................................ 424/400
See application file for complete search history.

(56) References Cited

U.S. PATENT DOCUMENTS

| 7,354,924 B2 | 4/2008 | Wang et al. |
| 7,745,625 B2 | 6/2010 | Ueda et al. |
| 8,268,885 B2 | 9/2012 | Van Acker et al. |
| 2005/0181041 A1* | 8/2005 | Goldman ............... 424/456 |
| 2005/0209246 A1* | 9/2005 | Ueda et al. ........... 514/253.04 |
| 2010/0056540 A1 | 3/2010 | Brown et al. |

* cited by examiner

*Primary Examiner* — Mina Haghighatian
*Assistant Examiner* — Luke Karpinski
(74) *Attorney, Agent, or Firm* — Dilworth IP, LLC; John F. Levis

(57) ABSTRACT

A process for the production of a formulation of HIV attachment inhibitor piperazine tris salt prodrug compound involves dissolving the prodrug compound in a solvent to form a solution; adding a first quantity of a first anti-solvent to the solution; then dispersing a first quantity of HPMC in the solution; adding a second quantity of the first anti-solvent to the solution; dispersing a second quantity of HPMC in the solution; then adding a second anti-solvent to the solution so as to crystallize the compound with the HPMC and thereby form the formulation, wherein the second anti-solvent is a combination of acetone and isopropyl acetate (IPAC). The formulation is then washed, and dried.

21 Claims, 8 Drawing Sheets

CO-PROCESSING METHOD AND FORMULATIONS FOR HIV ATTACHMENT INHIBITOR PRODRUG COMPOUND AND EXCIPIENTS

CROSS REFERENCE TO RELATED APPLICATION

This non-provisional application claims the benefit of U.S. Provisional Application Ser. No. 61/578,689 filed Dec. 21, 2011.

FIELD OF THE INVENTION

The present invention relates to a process for the production of an HIV attachment inhibitor compound formulation with excipients, and more specifically, to a process for producing a diketo piperazine-based prodrug attachment inhibitor compound embedded with one or more excipients in spherical-shaped agglomerates having improved physical characteristics. The invention also relates to the crystallized formulation so produced.

BACKGROUND OF THE INVENTION

HIV-1 (human immunodeficiency virus-1) infection remains a major medical problem, with an estimated 45-50 million people infected worldwide at the end of 2011. The number of cases of HIV and AIDS (acquired immunodeficiency syndrome) has risen rapidly. In 2005, approximately 5.0 million new infections were reported, and 3.1 million people died from AIDS. Currently available drugs for the treatment of HIV include nucleoside reverse transcriptase (RT) inhibitors: zidovudine (or AZT or RETROVIR®), didanosine (or VIDEX®), stavudine (or ZERIT®), lamivudine (or 3TC or EPIVIR®), zalcitabine (or DDC or HIVID®), abacavir succinate (or ZIAGEN®), Tenofovir disoproxil fumarate salt (or VIREAD®), emtricitabine (or FTC-EMTRIVA®), COMBIVIR® (contains -3TC plus AZT), TRIZIVIR® (contains abacavir, lamivudine, and zidovudine), Epzicom (contains abacavir and lamivudine), TRUVADA® (contains VIREAD® and EMTRIVA®); non-nucleoside reverse transcriptase inhibitors: rilpivirine (or Edurant), nevirapine (or VIRAMUNE®), delavirdine (or RESCRIPTOR®) and efavirenz (or SUSTIVA®), Atripla (TRUVADA®+SUSTIVA®), Complera (TRUVADA®+Edurant), and etravirine, and peptidomimetic protease inhibitors or approved formulations: saquinavir, indinavir, ritonavir, nelfinavir, amprenavir, lopinavir, KALETRA® (lopinavir and Ritonavir), darunavir, atazanavir (REYATAZ®) and tipranavir (APTIVUS®), and integrase inhibitors such as raltegravir (Isentress), and entry inhibitors such as enfuvirtide (T-20) (FUZEON®) and maraviroc (Selzentry). Other drugs are slated for approval within the next few years, or are earlier on in various stages of development.

In addition to the foregoing, HIV attachment inhibitors are a novel subclass of antiviral compounds that bind to the HIV surface glycoprotein gp120, and interfere with the interaction between the surface protein gp120 and the host cell receptor CD4. Thus, they prevent HIV from attaching to the human CD4 T-cell, and block HIV replication in the first stage of the HIV life cycle. The properties of HIV attachment inhibitors have been improved in an effort to obtain compounds with maximized utility and efficacy as antiviral agents.

One HIV attachment inhibitor compound, in particular, has now shown considerable prowess against HIV. This compound is known as 1-(4-benzoyl-piperazin-1-yl)-2-[4-methoxy-7-(3-methyl-[1,2,4]triazol-1-yl)-1H-pyrralo[2,3-c]pyridine-3-yl]-ethane-1,2-dione, which is set forth and described in U.S. Pat. No. 7,354,924, which is incorporated herein in its entirety:

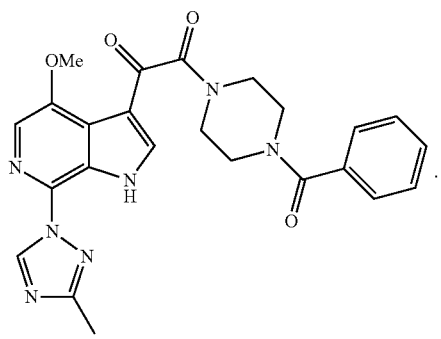 [SMILES: COc1cnc(-n2cnc(C)n2)c2[nH]cc(C(=O)C(=O)N3CCN(C(=O)c4ccccc4)CC3)c12]

Further, a phosphate ester prodrug of the above parent compound has now been developed. This compound is 1-benzoyl-4-[2-[4-methoxy-7-(3-methyl-1H-1,2,4-triazol-1-yl)-1-[phosphonooxy)methyl]-1H-pyrrolo[2,3-c]pyridin-3-yl]-1,2-dioxoethyl]-piperazine. It is set forth and described in U.S. Pat. No. 7,745,625, which is incorporated by reference herein it its entirety. The compound is represented by the formula below:

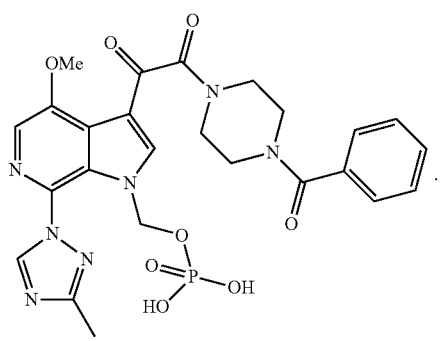 [SMILES: COc1cnc(-n2cnc(C)n2)c2c1c(C(=O)C(=O)N1CCN(C(=O)c3ccccc3)CC1)cn2COP(=O)(O)O]

A formulation with the above phosphate ester prodrug in tris salt form, together with hydroxypropyl methyl cellulose (HPMC), has been set forth and described in U.S. Publication No. 2010/0056540 A1, also incorporated by reference herein.

In certain other instances, however, there have been issues with formulating the API prodrug with excipients. The crystalline form of the input, unprocessed prodrug is typically characterized by highly chargeable, fragile needles with high aspect ratio, low bulk density and very poor flow capability, whether as API alone or when further mixed with excipients. Comparative FIG. 1 is a photograph of the unprocessed, crystalline phosphate ester prodrug compound. These characteristics can present significant challenges with either dry or wet granulation techniques. For dry granulation, poor powder flow presents a major challenge in controlling the hopper flow and feed into the roller compactor. With wet granulation, it has been difficult to control the change in form associated with the overall process, thereby often resulting in poor stability of the final product formulation.

What is now needed in the art is a new processing method for formulating the HIV attachment inhibitor phosphate ester prodrug compound with excipients, including HPMC. This method should produce a formulation with high API content with good release characteristics, as well as good flow, improved bulk density, and high compactability.

SUMMARY OF THE INVENTION

In a first embodiment, the invention is directed to a process for the production of a formulation of HIV attachment inhibitor piperazine tris salt prodrug compound, comprising:

a) dissolving said prodrug compound in a solvent to form a solution;

b) adding a first quantity of a first anti-solvent to said solution;

c) dispersing a first quantity of HPMC in said solution;

d) adding a second quantity of said first anti-solvent to said solution;

e) dispersing a second quantity of HPMC in said solution; and f) adding a second anti-solvent to said solution so as to crystallize said compound with said HPMC and thereby form said formulation, wherein said second anti-solvent is a combination consisting essentially of acetone and isopropyl acetate (IPAC).

It is further preferred that the next step comprise the filtering and washing of the crystallized compound/HPMC with an additional amount of the first anti-solvent, followed by agitated drying in vacuum to remove substantially all used solvents.

In a further embodiment, the invention is directed to a process for the production of a formulation of HIV attachment inhibitor piperazine tris salt prodrug compound, comprising:

a) adding a first anti-solvent to a first vessel;

b) dispersing HPMC in said first vessel;

c) dissolving said prodrug compound in a solvent to form a solution, and adding said solution to said first vessel;

d) adding a second anti-solvent to said solution in said first vessel so as to crystallize said compound with said HPMC and thereby form said formulation, wherein said second anti-solvent is a combination consisting essentially of acetone and isopropyl acetate (IPAC). In this embodiment, the next step involves filtering and washing of the crystallized compound/ HPMC, followed by agitated drying to remove substantially all solvents.

The invention is further directed to the formulation so produced by the processes herein set forth.

In a further embodiment, the invention is also directed to the use of the formulation for producing pharmaceutical grade tablets.

The present invention is directed to these, as well as other important ends, hereinafter described.

DETAILED DESCRIPTION OF THE EMBODIMENTS

Figure 1:
FIG. 1 (comparative) is a scanning electron microscope (SEM) image of input, unprocessed API HIV attachment inhibitor piperazine phosphate ester prodrug compound at 650× magnification.

While a range of alternative water soluble salts of the phosphate ester prodrug may be employed, the tris salt form of 1-benzoyl-4-[2-[4-methoxy-7-(3-methyl-1H-1,2,4-triazol-1-yl)-1-[(phosphonooxy)methyl]-1H-pyrrolo[2,3-c]pyridin-3-yl]-1,2-dioxoethyl]-piperazine,in particular, is preferred for use herein.

The prodrug is first dissolved in a solvent so as to form a solution. The solvent is preferably water in the range of about 1.67 to 2.67 volume (mL) with respect to the prodrug weight (grams).

Next, a first quantity of a first anti-solvent is added to the prodrug solution. This first anti-solvent is preferably acetone in the range of about 4.0 to 5.0 volume (mL), more preferably about 4.66 volume (mL), with respect to the prodrug weight (grams). Those skilled in the art may find that acetonitrile is one possible alternative as a first anti-solvent herein.

Thereafter, a first quantity of HPMC is dispersed in the solution. The first quantity of HPMC will preferably be approximately 40-60%, and even more preferably, about 50% of the total amount of HPMC utilized in the co-processing method with the phosphate ester prodrug. It is further preferred that the ratio of the prodrug compound to the HPMC after the method of the invention is completed be about 3:1. Put another way, the HPMC will comprise about 20-30% of the final formulation, more preferably about 25% thereof. After addition of the HPMC, the solution is preferably allowed to stand for at least 20 minutes, and more preferably, up to about an hour or so.

A second quantity of the first anti-solvent of about 4.0 to 5.0 volume (mL), more preferably about 4.66 volume (mL), with respect to the prodrug weight (grams) is then added to the prodrug solution containing the dispersed HPMC.

Next, the remaining HPMC is dispersed in the solution. This quantity represents about 60-40%, and even more preferably, about 50% of the total amount of HPMC utilized herein. Again, the solution containing the HPMC is preferably allowed to stand or age for 20 minutes, and preferably, for up to an hour or so.

At this point, a second anti-solvent with the quantity of about 11.0 to 12.0 volume (mL), more preferably about 11.65 volume (mL), with respect to the prodrug weight (grams) is added to the solution containing the prodrug and dispersed HPMC. The second anti-solvent is a mixture of acetone and isopropyl acetate (IPAC). Preferably, the mixture is about 22:78 to 18:82 v/v acetone:IPAC, and even more preferably, about 20:80 v/v acetone:IPAC ratio. The second anti-solvent should be substantially free of additional compounds, for example, compounds such as ethyl acetate and n-butyl acetate. Both the particular combination of the second anti-solvents utilized, and their respective ratios, are important aspects of the method herein. The second anti-solvent is added to the solution over the course of approximately 1 to 5 hours. Upon addition of the second anti-solvent, the entire solution is slowly agitated and allowed to age for an extended period, preferably no less than about 12 hours, and more preferably, for about 16 hours. Without being bound by any particular theory, it appears that this extended time period permits the growth of prodrug crystals on the inside and on the surface of the HPMC polymers.

Finally, the prodrug and HPMC slurry mixture is diluted with acetone and filtered on a filter dryer. The formulation mixture is again washed, preferably twice washed, preferably with acetone. Thereafter, the formulation may be densified for several minutes under agitation. The formulation is then allowed to either tray dry under vacuum, or dry with optional agitation. The formulation may then be sieved or co-milled using apparatus and procedures available in the art.

Figure 2A:
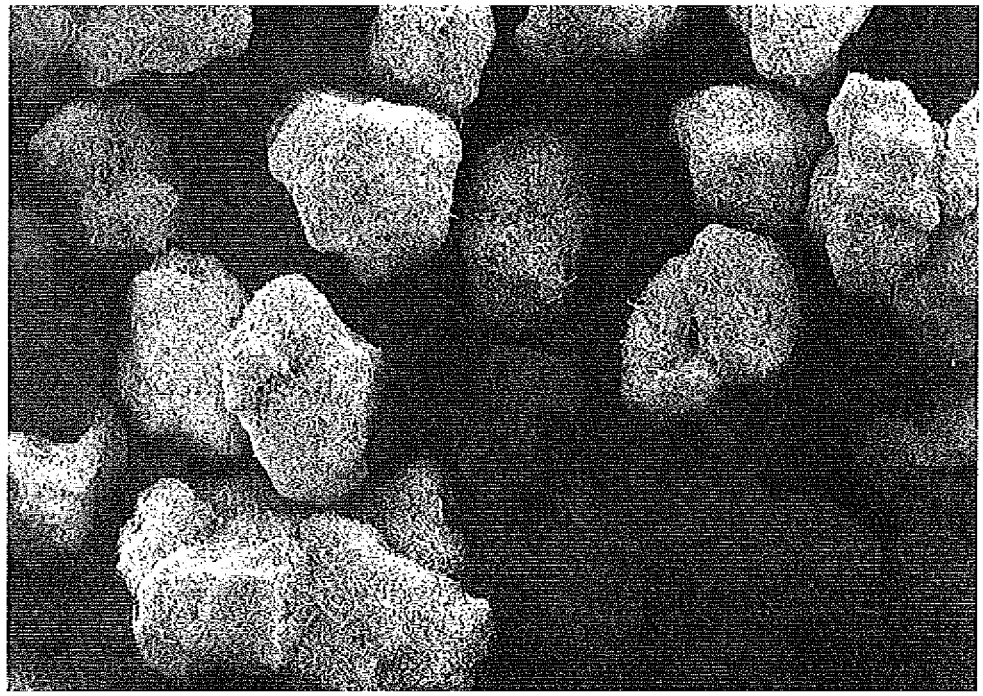
FIG. 2A is a SEM image of tray-dried prodrug/ HPMC formulation at 50× magnification according to an embodiment of the invention.
Figure 2B:
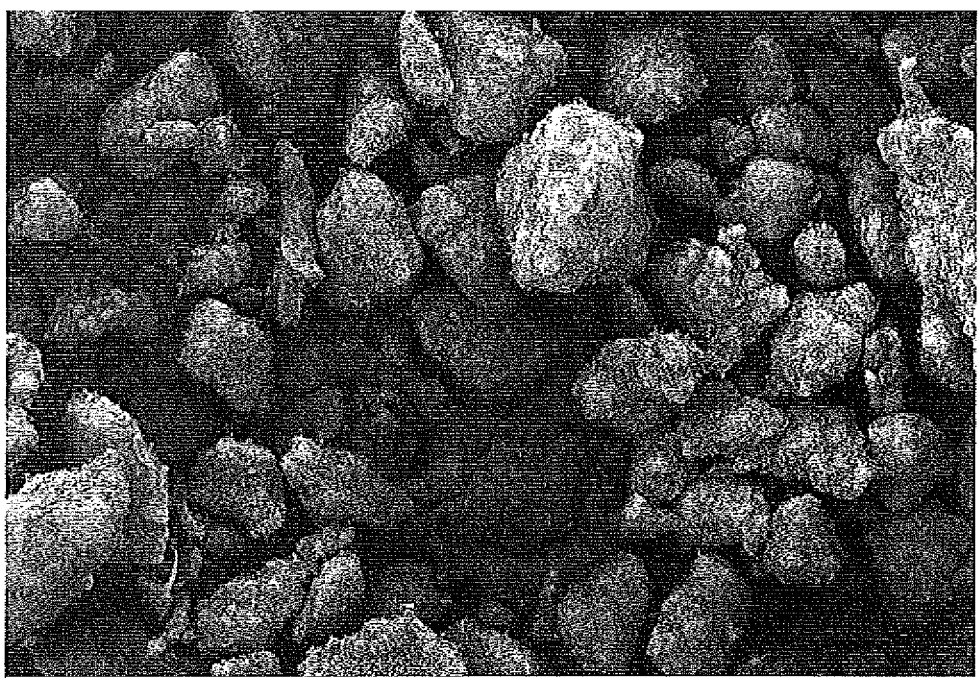
FIG. 2B is a SEM image of agitation-dried prodrug/HPMC formulation at 50× magnification according to a further embodiment of the invention.
Figure 3A:
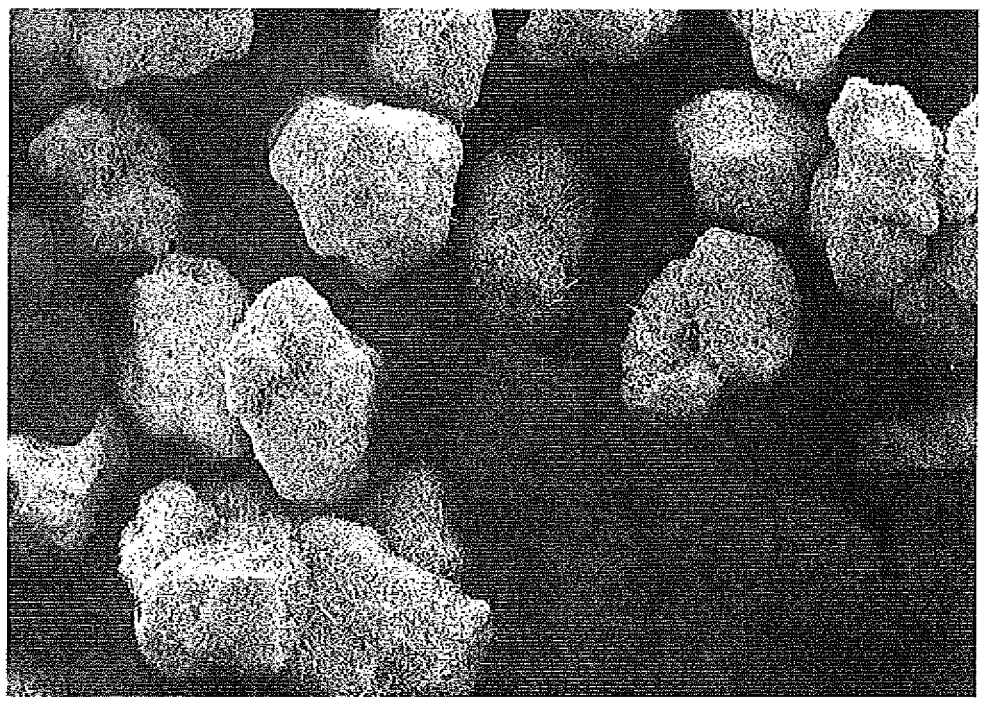
FIG. 3A is the same image presented in FIG. 2A for comparison purposes with FIGS. 3B and 3C below.
Figure 3B:
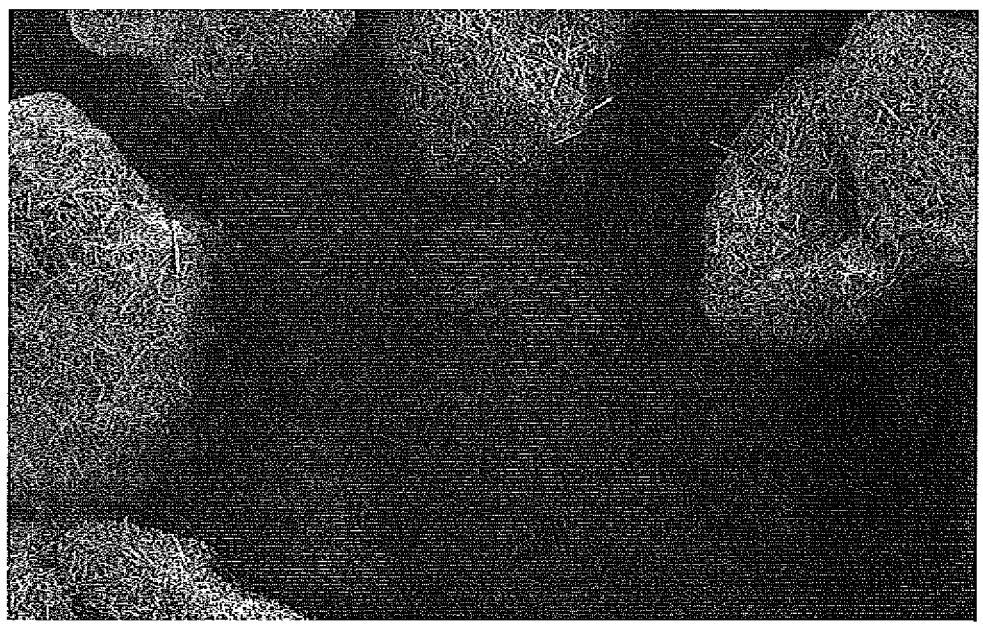
FIG. 3B is a SEM image of the formulation shown in FIG. 3A, but at 100× magnification.
Figure 3C:
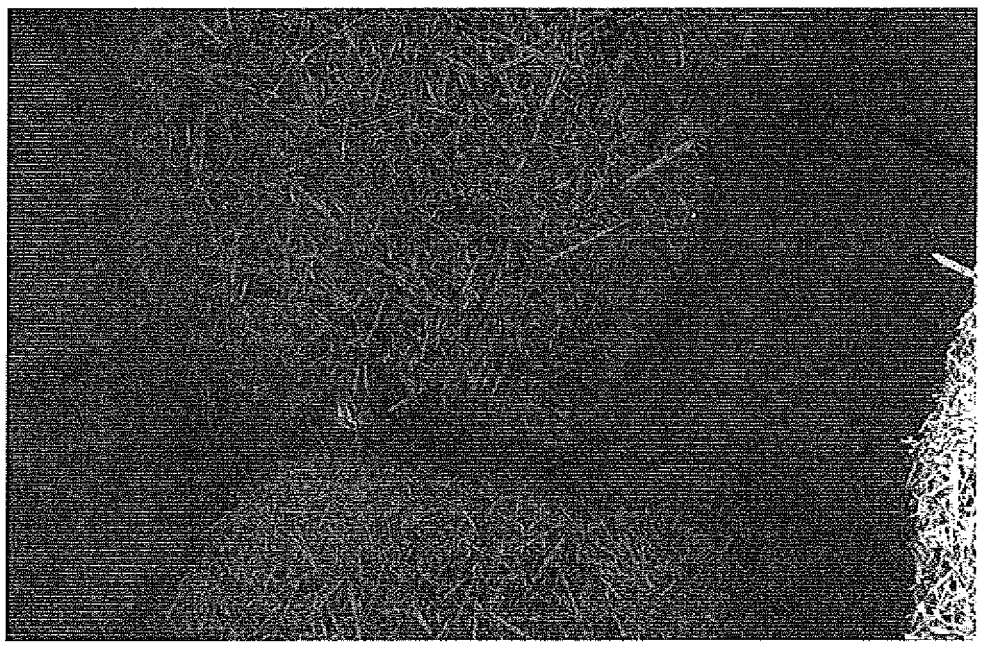
FIG. 3C is a SEM image of the formulation shown in FIG. 3A, but at 250× magnification.
Figure 4A:
FIG. 4A is a SEM image of the surface of the formulation set forth in FIG. 3A showing individual needles at 1000× magnification.
Figure 4B:
FIG. 4B is a SEM image of the formulation shown in FIG. 4A at 2500× magnification.
Figure 4C:
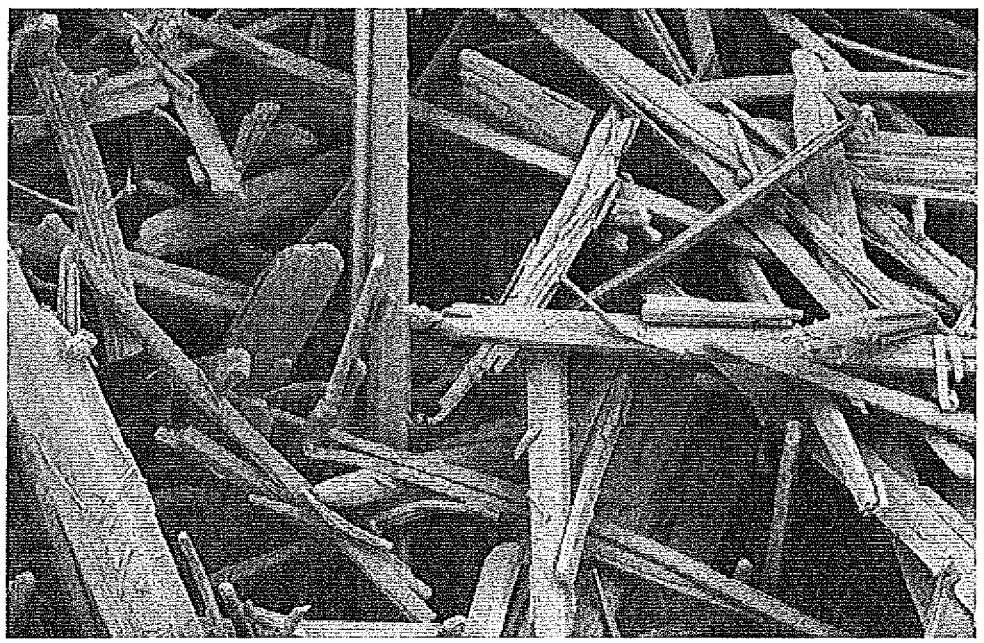
FIG. 4C is a SEM image of the formulation shown in FIG. 4A at 5000× magnification.

FIG. 2A shows the resulting formulation after it has been tray dried, while FIG. 2B shows a similar formulation after agitation drying. FIGS. 3A, 3B and 3C illustrate the formulation of the invention at progressively higher magnification. The spherical-shaped agglomerates are clearly shown in each scanning electron microscope image. FIGS. 4A, 4B and 4C illustrate the individual crystallized needles present in the formulation agglomerates. In particular, the images of FIGS. 4A-4C should be contrasted with the image presented in FIG. 1.

Figure 5A:
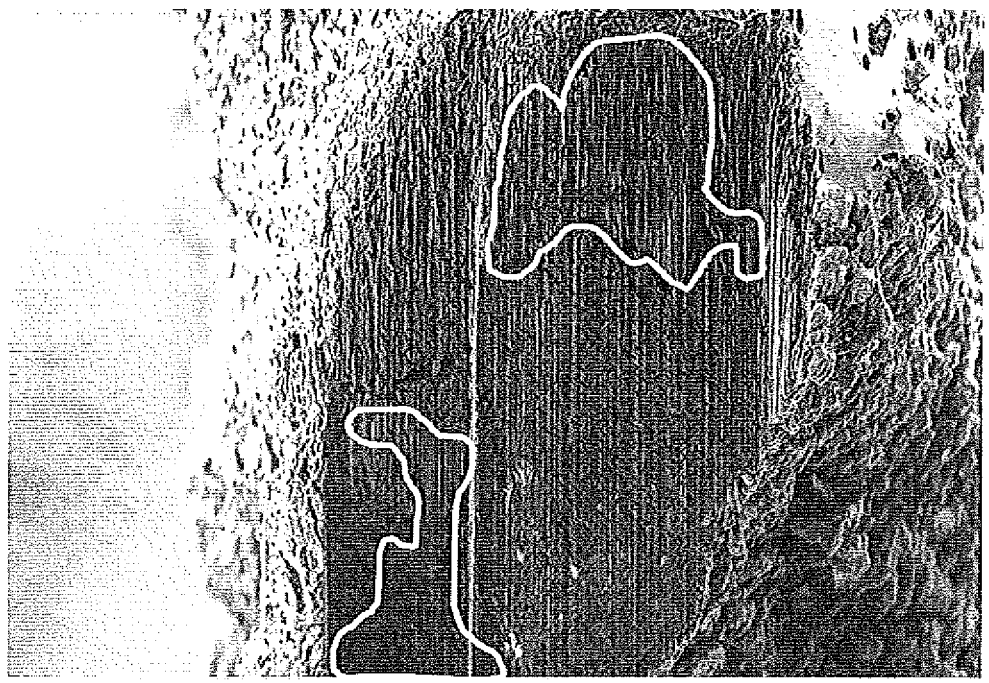
FIG. 5A is a FLB-SEM cross-sectional image of the formulation of the invention according to one embodiment at 696× magnification.
Figure 5B:
FIG. 5B is a FIB-SEM surface image of the formulation of the invention set forth in FIG. 5A at 4340× magnification.
Figure 6A:
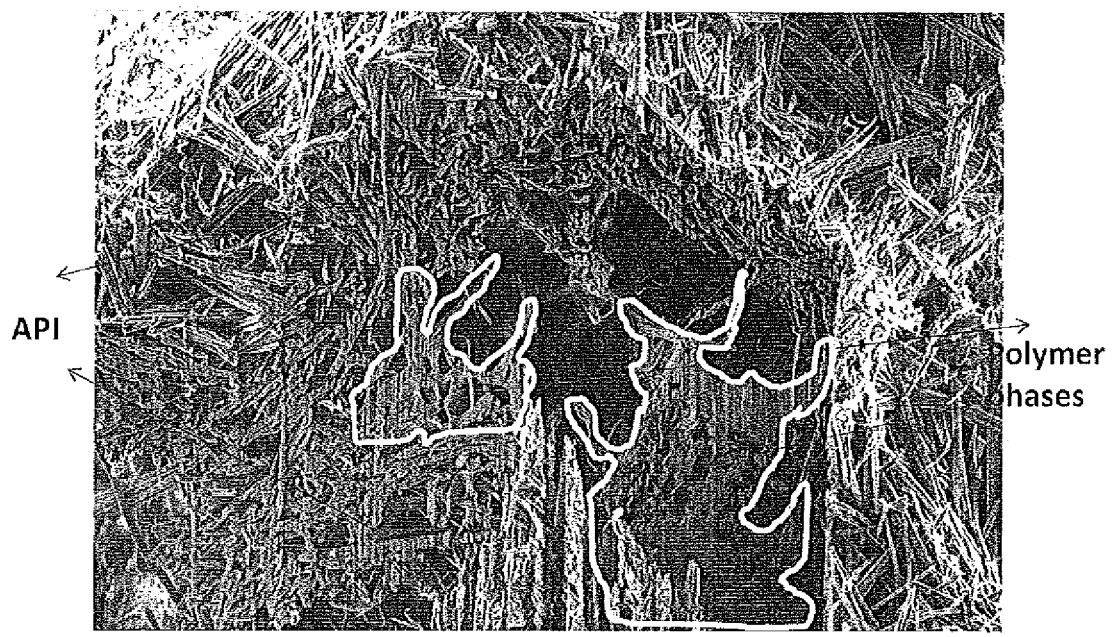
FIG. 6A is a FIB-SEM cross-sectional image of the formulation of the invention according to a further embodiment at 500× magnification.
Figure 6B:
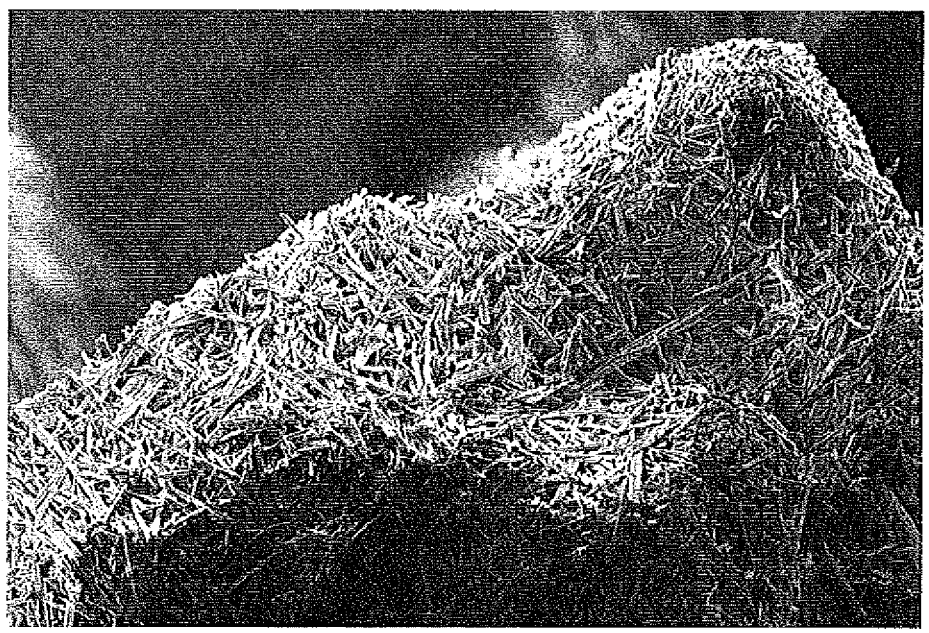
FIG. 6B is a FIB-SEM surface image of the formulation of the invention as set forth in FIG. 6A at 500× magnification.

As set forth above, in some embodiments it may be preferable to allow the formulation to densify and dry under agitation. FIGS. 5A and 5B illustrate the composition profile of the formulation under agitated drying. FIGS. 6A and 6B, while also part of the invention, illustrate the slightly less preferred method of tray drying without agitation. All the FIGS. 5 and 6 were characterized by FIB-SEM (focused ion beam SEM). The FIB-SEM instrument applies a high energy ion beam to carve out the surface of a sample particle, and then applies an X-ray probe to scan the element composition on the inner surface to obtain a cross-sectional composition profile. The FIB-SEM characterization indicates two points: 1) the API needles are embedded inside and on the surface of a skeleton structure formed by the HPMC; and 2) the tray dried particles have more voids inside the structure, while the particles from agitated drying are more closely packed with less observable voids. In both FIGS. 5A and 6A, the polymer phases are outlined in bold. In addition, in FIG. 6A, the API is indicated with arrows.

EXAMPLES

The following examples illustrate preferred aspects of the invention, but should not be construed as limiting the scope thereof:

Example 1

105 gm Scale as an Example
Crystallization Steps:
 1. Dissolve 105.0 g API in 245 ml DI water in a 4 L reactor,
 2. Dilute by 490 ml acetone agitate at 160 rpm and 35° C.
 3. Slowly add in 21 g HPMC at agitation 160 rpm and 35° C.
   (Note: Avoid forming any lumps of polymer in the suspension when adding polymer.)
 4. Wait for 30 min., then add 490 ml acetone in 5 min (~100 ml/min) with 160 rpm agitation.
 5. Add 14 g HPMC (same lot) and agitate at 125 rpm for 30 min.
 6. Add 1225 ml acetone/IPAC (1:4) in 280 min (addition rate 4.4 ml/min) starting at 45° C. and with agitator speed at 100-105 rpm.
   (Note: Scale-up based on mixing time of 70 min from 15 g. batch, and 4× longer needed to scale-up from 70 ml to 2450 ml working volume.)
 7. Bath temp lowered from 45° C. to 20° C. in 280 min during acetone/IPAC addition (cooling rate 25° C./280 min).
 8. After addition of all acetone/IPAC solvent, age the slurry at 20° C. and with 90-95 rpm agitation for 12-16 hr.
 9. Retain slurry for HPLC and Karl-Fisher instrument, retain ML (mother liquor) and wash liquid for yield check.

Example 2

Alternatively, the crystallization sequence can be changed as another example depicted below:
 1. Add 980 mL acetone (as first anti-solvent) to a 4 L reactor.
 2. Add 35 g HPMC and agitate at 160 RPM at 45C.
 3. Dissolve 105.0 g API in 245 ml DI water in separate vessel, add solution to reactor.
 4. Wait 40 min.
 5. Add 1225 ml acetone/IPAC (1:4) (as second anti-solvent) in 280 min (addition rate 4.4 ml/min) starting at 45° C. and with agitator speed at 100-105 rpm.
   (Note: Scale-up based on mixing time of 70 min from 15 g. batch, and 4× longer needed to scale-up from 70 ml to 2450 ml working volume.)
 6. Bath temp lowered from 45° C. to 20° C. in 280 min during acetone/IPAC addition (cooling rate 25° C./280 min).
 7. After addition of all acetone/IPAC solvent, age the slurry at 20° C. and with 90-95 rpm agitation for 12-16 hr.
 8./9. Retain slurry for HPLC and Karl-Fisher instrument, retain ML (mother liquor) and wash liquid for yield check.
Filtration
 10. Charge 315 ml acetone to the slurry in the crystallizer while agitating.
Agitate for 2-3 minutes.
 11. Filter slurry.
 12. Deliquor the cake completely. Do not blow dry.
 13. Reslurry wash with 525 ml acetone. Agitate for 5-10 min at 10-40 rpm.
 14. Deliquor the cake completely. Do not blow dry.
 15. Displacement wash with 210 ml acetone.
 16. Deliquor the cake completely. Do not blow dry.
Densification
 17. Agitate the cake.
   RPM=10-40, agitate by lowering and raising agitator for complete mixing at RPM=3-10 rpm.
   Continue agitation until cake volume is constant (10-30 minutes).
Drying
 18. Vacuum dry with periodic agitation.
   Ramp the jacket temperature from 25° C. to up to 50° C. over 2-4 hrs.
   Agitate for 2-5 minutes every 15 to 30 minutes until dry.
   Dry until LOD (loss on drying)<3% LOD.

The ester phosphate prodrug formulation obtained according to the various process embodiments herein described contains very high API content. The formulation is also characterized by improved bulk density, good flow characteristics and high compactability. When further compressed and formulated into tablets using methods and apparatus available in the art, the resulting tablets exhibit excellent extended release properties. Characterization results from Example 1 (Batches 1-5) to reflect the formulation properties from typical batches are provided below for illustration.

| Batch | Scale (kg) | Bulk Density (g/cc) | Tapped Density (g/cc) | Flow (s/100 g) | Volumetric Flow (mL/s) |
|---|---|---|---|---|---|
| API | 120 | 0.13 | 0.23 | incomplete | incomplete |
| 1 | 0.5 | 0.31 | 0.40 | 19.1 | 17.0 |
| 2 | 0.5 | 0.39 | 0.48 | 12.8 | 19.9 |
| 3 | 3.8 | 0.30 | 0.39 | 26.7 | 12.4 |
| 4 | 3.8 | 0.34 | 0.43 | 24.2 | 12.3 |
| 5 | 14.5 | 0.33 | 0.43 | 33.6 | 9.2 |

The foregoing description is merely illustrative and should not be understood to limit the scope or underlying principles of the invention in any way. Indeed, various modifications of the invention, in addition to those shown and described herein, will become apparent to those skilled in the art from the foregoing description and examples. Such modifications are also intended to fall within the scope of the appended claims.

What is claimed is:

1. A process for the production of a formulation of HPMC and a crystalline HIV attachment inhibitor piperazine tris salt prodrug compound, wherein said compound is 1-benzoyl-4-[2-[4-methoxy-7-(3-methyl-1H-1,2,4-triazol-1-yl)-1-[(phosphonooxy)methyl]-1H-pyrrolo[2,3-c]pyridin-3-yl]-1,2-dioxoethyl]-piperazine, said process comprising:
    a) dissolving said prodrug compound in water to form a solution;
    b) adding a first quantity of a first anti-solvent to said solution, wherein said first anti-solvent is acetone;
    c) dispersing a first quantity of HPMC in said solution;
    d) adding a second quantity of said first anti-solvent to said solution;
    e) dispersing a second quantity of HPMC in said solution; and
    f) adding a second anti-solvent to said solution so as to crystallize said compound on the inside and on the surface of said HPMC and thereby form said formulation, wherein said second anti-solvent is a combination consisting essentially of acetone and isopropyl acetate (IPAC).

2. The process of claim 1, further comprising the steps of filtering, washing and drying said formulation.

3. The process of claim 1, wherein said first quantity of HPMC is approximately 40 to 60% of the total quantity.

4. The process of claim 1, wherein said second anti-solvent is a combination of acetone and IPAC in about a 20:80 v/v ratio.

5. The process of claim 4, wherein said second anti-solvent is free of additional compounds.

6. The process of claim 5, wherein said additional compounds comprise ethyl acetate and n-butyl acetate.

7. The process of claim 2, wherein said filtering and washing is done with acetone.

8. The process of claim 7, wherein said drying is done under agitation.

9. The process of claim 8, wherein said formulation has improved powder flow and compactability.

10. The process of claim 9, wherein said formulation is in the form of spherical shaped agglomerates.

11. The process of claim 10, wherein said prodrug compound is crystallized within said HPMC.

12. The process of claim 1, wherein in step a) said prodrug compound is crystalline and is characterized by highly chargeable, fragile needles with high aspect ratio and poor flow characteristics.

13. The process of claim 4, wherein in step f) said second anti-solvent is added over the course of approximately 1 to 5 hours.

14. The process of claim 1, wherein after step f) the ratio of said prodrug compound to said HPMC is approximately 3:1.

15. The formulation obtained according to the process of claim 1.

16. A process for the production of a formulation of HPMC and a crystalline HIV attachment inhibitor piperazine tris salt prodrug compound, wherein said compound is 1-benzoyl-4-[2-[4-methoxy-7-(3-methyl-1H-1,2,4-triazol-1-yl)-1-[(phosphonooxy)methyl]-1H-pyrrolo[2,3-c]pyridin-3-yl]-1,2-dioxoethyl]-piperazine, said process comprising:
    a) adding a first anti-solvent to a first vessel, wherein said first anti-solvent is acetone;
    b) dispersing HPMC in said first vessel;
    c) dissolving said prodrug compound in water to form a solution, and adding said solution to said first vessel;
    d) adding a second anti-solvent to said solution in said first vessel so as to crystallize said compound on the inside and on the surface of said HPMC and thereby form said formulation, wherein said second anti-solvent is a combination consisting essentially of acetone and isopropyl acetate (IPAC).

17. The formulation obtained according to the process of claim 16.

18. The process of claim 1, wherein said added quantities of HPMC form a slurry in said solution.

19. The process of claim 1, wherein after addition of said second anti-solvent the said solution is slowly agitated and allowed to age for an extended period to facilitate said crystallization of said prodrug compound.

20. The process as claimed in claim 19, wherein said extended period is for no less than about 12 hours.

21. The process as claimed in claim 20, wherein said extended period is about 16 hours.

* * * * *